(12) United States Patent  
Engelbart et al.

(10) Patent No.: US 7,171,033 B2  
(45) Date of Patent: Jan. 30, 2007

(54) SYSTEM AND METHOD FOR IDENTIFYING DEFECTS IN A COMPOSITE STRUCTURE

(75) Inventors: Roger W. Engelbart, St. Louis, MO (US); Scott T. Holmes, Oxford, PA (US); Craig Walters, Wentzville, MO (US)

(73) Assignee: The Boeing Company, Seattle, WA (US)

( * ) Notice: Subject to any disclaimer, the term of this patent is extended or adjusted under 35 U.S.C. 154(b) by 915 days.

(21) Appl. No.: 09/819,922

(22) Filed: Mar. 28, 2001

(65) Prior Publication Data

US 2002/0141632 A1    Oct. 3, 2002

(51) Int. Cl.  
*G06K 9/00* (2006.01)

(52) U.S. Cl. ..................................... 382/141
(58) Field of Classification Search ................ 382/141, 382/143–153; 348/86–92, 125, 127; 356/237.1, 356/239.1, 430; 73/865.8; 250/559.15; 700/124  
See application file for complete search history.

(56) References Cited

U.S. PATENT DOCUMENTS

| | | | |
|---|---|---|---|
| 3,243,509 A | 3/1966 | Stut | |
| 4,064,534 A | 12/1977 | Chen et al. | |
| 4,120,402 A | 10/1978 | Swanson | |
| 4,135,204 A | 1/1979 | Davis et al. | |
| 4,415,811 A * | 11/1983 | Beck et al. | ............ 250/559.15 |
| 4,437,115 A | 3/1984 | Yoshida | |
| 4,445,185 A | 4/1984 | Davis, Jr. et al. | |
| 4,760,444 A | 7/1988 | Nielson et al. | |
| 5,007,096 A | 4/1991 | Yoshida | |
| 5,016,099 A | 5/1991 | Bongardt et al. | |
| 5,058,174 A | 10/1991 | Carroll | |
| 5,058,497 A | 10/1991 | Bishop et al. | |
| 5,187,573 A | 2/1993 | Yoshida | |
| 5,237,407 A | 8/1993 | Crezee et al. | |
| 5,253,302 A | 10/1993 | Massen | |
| 5,258,917 A | 11/1993 | Bruder et al. | |
| 5,263,094 A | 11/1993 | Laitinen et al. | |
| 5,331,312 A | 7/1994 | Kudoh | |
| 5,333,208 A | 7/1994 | Massen | |
| 5,359,525 A * | 10/1994 | Weyenberg | .................. 700/124 |
| 5,426,509 A | 6/1995 | Peplinski | |
| 5,440,650 A | 8/1995 | Hieda et al. | |

(Continued)

OTHER PUBLICATIONS

*Material Selection/Fabrication Issues for Thermoplastic Fiber Placement*, Journal of Thermoplastic Composite Materials, vol. 8, pp. 2-7 (Technomic Publishing Co., Inc.) (1995).

(Continued)

*Primary Examiner*—Vikkram Bali  
(74) *Attorney, Agent, or Firm*—Alston & Bird LLP

(57) ABSTRACT

A system and method for identifying defects in a composite structure is provided. The system includes a camera for receiving images of the composite structure, a processor for manipulating the images and outputting a response based on the images, and a light source for illuminating the composite structure. Advantageously, the light source is positioned at an oblique angle relative to the composite structure and comprises an infrared component that is differently reflected by defects in the composite structure than from portions of the composite structure that are defect free. Based on the response provided by the processor, defects that meet predetermined criteria can be identified.

39 Claims, 5 Drawing Sheets

U.S. PATENT DOCUMENTS

| | | |
|---|---|---|
| 5,452,370 A | 9/1995 | Nagata |
| 5,486,819 A | 1/1996 | Horie |
| 5,513,537 A * | 5/1996 | Brooks et al. ............. 73/865.8 |
| 5,533,628 A | 7/1996 | Tao |
| 5,646,682 A | 7/1997 | Sogabe et al. |
| 5,652,432 A | 7/1997 | Yaginuma |
| 5,700,337 A | 12/1997 | Jacobs et al. |
| 5,732,147 A | 3/1998 | Tao |
| 6,005,965 A * | 12/1999 | Tsuda et al. ................ 382/145 |
| 6,064,429 A | 5/2000 | Belk et al. |
| 6,295,129 B1 * | 9/2001 | Bjork ......................... 356/430 |
| 6,603,874 B1 * | 8/2003 | Stern et al. ................. 382/144 |

OTHER PUBLICATIONS

*Manufacturing of Smart Structures Using Fiber Placement Manufacturing Processes*; SPIE, vol. 2447, pp. 266-273 (1995).

*Fiber Placement Inspection System and Experimental Approach*; 43rd Int'l SAMPE Symposium, pp. 957-963 (Society for the Advancement of Material and Process Engineering) (1998).

\* cited by examiner

SYSTEM AND METHOD FOR IDENTIFYING DEFECTS IN A COMPOSITE STRUCTURE

GOVERNMENT RIGHTS

The United States Government may have rights in this invention pursuant to Contract No. F33615-98-C5104 awarded by the Department of the Air Force.

FIELD OF THE INVENTION

The present invention relates generally to the fabrication of composite structures, and more particularly to systems and methods adapted for locating defects during fabrication of composite structures.

BACKGROUND OF THE INVENTION

Composite structures have been known in the art for many years. Although composite structures can be formed in many different manners, one advantageous technique for forming composite structures is a fiber placement or automated collation process. According to conventional automated collation techniques, one or more ribbons of composite material (also known as composite tows) are laid down on a substrate. The substrate may be a tool or mandrel, but, more conventionally, is formed of one or more underlying layers of composite material which have been previously laid down and compacted. In this regard, conventional fiber placement processes utilize a heat source to assist in compaction of the plies of composite material at a localized nip point. In particular, the ribbon or tow of composite material and the underlying substrate are heated at the nip point to increase the tack of the resin of the plies while being subjected to compressive forces to ensure adhesion to the substrate. For example, the plies of composite material can be compacted by a compliant pressure roller as described by U.S. Pat. No. 5,058,497, which is incorporated herein by reference. To complete the part, additional strips of composite material can be applied in a side-by-side manner to form layers and can be subjected to localized heat and pressure during the consolidation process. Other conventional fiber placement process methods are described in U.S. Pat. No. 5,700,337, which is incorporated herein by reference.

Composite laminates that are fabricated by the fiber placement process are typically subjected to a 100% ply-by-ply visual inspection for such defects as tow gaps, overlaps and twists. Typcially, the inspection is performed manually by either an inspector or the fiber placement machine operator. The machine must be stopped and the process of laying materials halted until the inspection is complete. During the inspection, the operator verifies the dimensions of any suspect anomalies and quantifies the number of anomalies per given unit area. The anomalies are repaired as needed and laying of the next ply proceeds. However, the fabrication process has been disadvantageously slowed by the inspection process.

To overcome the disadvantages of manually inspecting a workpiece, machine inspection systems have employed video and other images that are processed by a computer to detect the existence of irregularities on an inspected object. For example, U.S. Pat. No. 4,760,444 discloses a machine visual inspection device having video inspection stations for determining the reflectance of different portions of a workpiece. A central processing unit then digitizes the reflectance values and stores the digitized values in memory. The computer also contains a standard image previously stored in memory that serves as a reference to the reflectance values. As such, the computer can compare the standard image to the digitized reflectance values to located any anomalies. However, this system provides only a single reference point when inspecting workpieces that cannot be modified by the operator.

Another inspection system is disclosed by U.S. Pat. No. 4,064,534, which discloses a television camera and logic circuitry to electronically compare the profile of an image of a workpiece against a standard image whereby the item being inspected or measured can either be rejected or accepted. More specifically, a video image of the workpiece is captured by a TV camera and converted into digital form for recording in a memory device. The recorded image is then compared against a standard image that is preloaded into memory. Based on the differences between the images, a processor determines whether the workpiece passes or fails. However, this system also requires that the standard measurements are preloaded into the computer and not controllable by the operator thereafter.

Yet another conventional inspection system employs a laser that is swept across a workpiece to identify locations on the workpiece where laser reflectivity changes. For example, a gap or other inconsistency would cause a change in the reflectivity of the surface. The reflectivity changes are then interpreted by a computer to identify defects.

However, each of these systems is susceptible to obtaining false readings due to glare or other problems caused by ambient lighting or by the laser-based scanning system. In this regard, conventional machine-based inspection systems lack a suitable lighting component that provides high contrast for defects located on the workpiece, while preventing ambient lighting and material reflectivity from hampering the identification of defects. This is further complicated during inspection of carbon materials by the appearance of black defects on a black background. In addition, conventional machine-based inspection systems do not readily permit the definition of defects or the viewing area to be altered in a controlled manner.

SUMMARY OF THE INVENTION

These and other needs are provided, according to the present invention, by a system and method for identifying defects in a composite structure during fabrication thereof having an infrared light source positioned at an oblique angle relative to the composite structure, wherein the light source causes defects in the composite structure to reflect light differently than the reflections from portions of the composite structure that are defect free. By using an obliquely-angled infrared light source, slight flaws typically undetected by conventional systems can be detected by the system and method of the present invention because the infrared component advantageously creates a high contrast between the defects and the other defect-free portions of the composite structure such that ambient lighting and associated reflectivity variations do not diminish the ability to detect defects.

More specifically, the system of identifying defects in a composite structure according to the present invention comprises a camera for receiving images of the composite structure which is comprised of a plurality of adjacent strips of composite tows or ribbons of tape. In one embodiment, the system also includes a processor for processing the images and outputting a response identifying the defect based on the images received by the camera. The system further includes a light source that is positioned at an oblique angle relative to the composite structure, which in one embodiment is about 45°, for illuminating the composite structure in such a way that the infrared component of the light source causes defects in the composite structure to reflect light differently than the reflections from portions of the composite structure that are defect free. In one embodiment, the light source is an infrared light. Other light sources may also be used, such as an incandescent light, as long as the light source provides a suitable infrared component. In one particularly advantageous embodiment, the light source comprises a plurality of light emitting diodes (LED), which may be arranged in an array or cluster formation. In yet another embodiment, the light source comprises two arrays positioned such that an acute angle is defined therebetween.

In one embodiment, the system according to the present invention also includes a marking device for indicating the location of the defects on the composite structure. More specifically, the marking device, such as an ink jet sprayer or similar device, receives instructions from the processor to mark a portion of the composite structure that includes a defect such that the defect is brought to the attention of the operator with respect to its precise location on the surface. Other marking devices can also be used, such as an audible alarm or the like.

In operation, the camera, which may be a video camera or a fiber optic camera, is capable of capturing images of the composite structure wherein the images comprise a plurality of pixels. According to the present invention, the captured images are black and white images ranging from a black through a plurality of shades of gray to white. The processor is capable of binarizing the images by setting all the pixels representing a color darker than a predetermined gray level to black and setting all the remaining pixels to white. Advantageously, the system allows the operator to adjust the binarization threshold and the image viewing area, such that the operator can control the size and magnitude of the defects represented by the plurality of pixels.

More specifically, defects in the composite layers are identified by positioning the camera proximate the composite structure and illuminating the composite structure with the obliquely-mounted light source. The camera and light source are moved across the composite structure, recording images of the composite structure along the way. The images are processed to identify the defects in the composite structure. In one embodiment, the camera is positioned perpendicular to the composite structure. The infrared light source illuminates the composite structure in such a way that defects in the composite structure, such as particles and/or gaps, can be recorded by the system and processed according to the defect tolerance created by the operator. Advantageously, even slight defects, which in conventional systems would be interpreted as an undetectable black defect on a black background, can be detected and identified to the operator.

Thus, the present invention provides a system and method for identifying defects in a composite structure by providing an obliquely-mounted light source having an infrared component such that defects in the composite structure will be more readily detectable. As a result, the system and method permit the operator to correct defects which would otherwise go undetected and create structural flaws or inconsistencies that may affect the integrity of the composite structure. As such, less material is wasted during the fabrication process and a lower cost per pound of material for the composite structure is realized.

BRIEF DESCRIPTION OF THE DRAWINGS

Some of the advantages of the present invention having been stated, others will appear as the description proceeds, when considered in conjunction with the accompanying drawings, which are not necessarily drawn to scale, in which.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
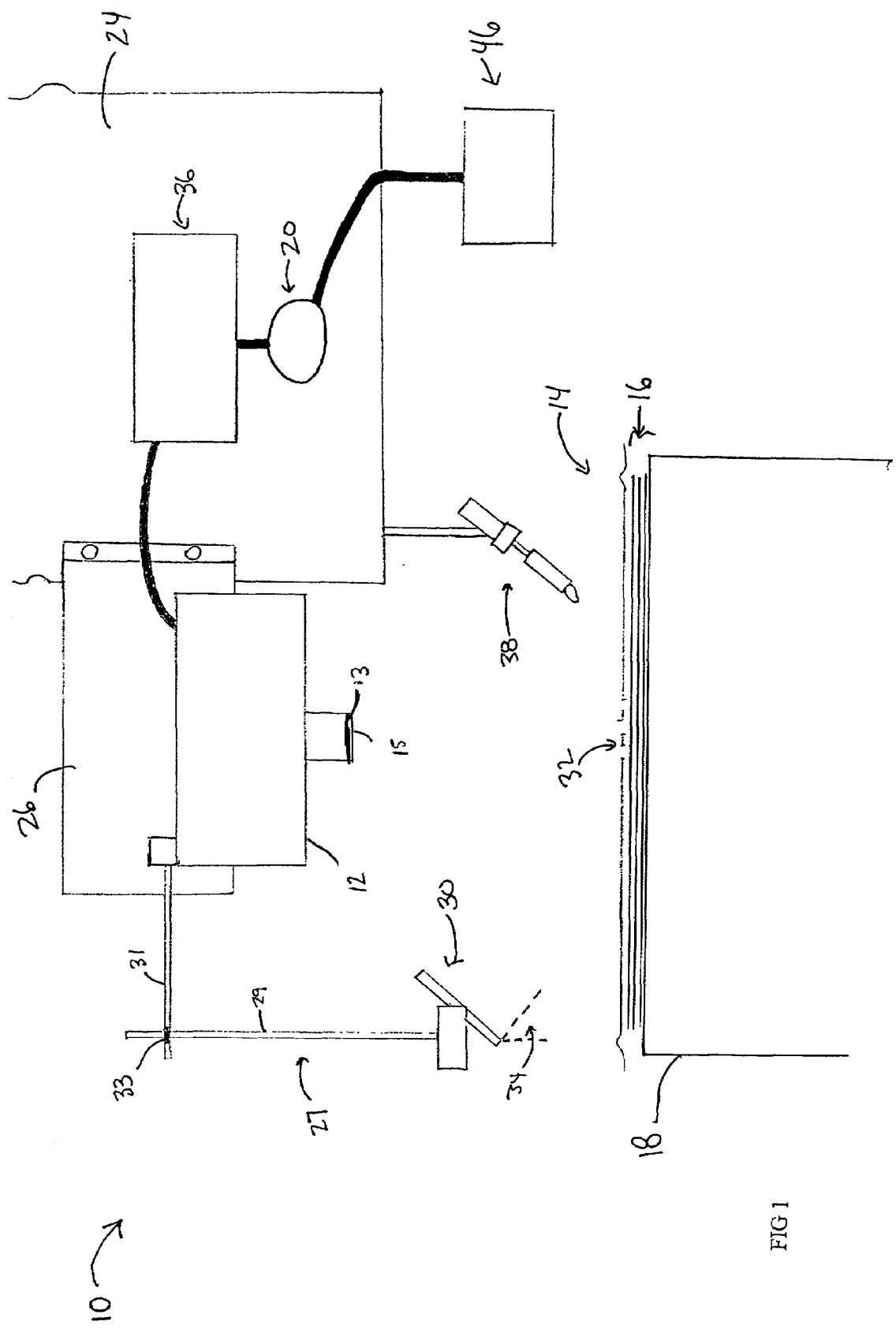
FIG. 1 is a schematic view of a system for identifying defects in a composite structure during fabrication thereof according to one embodiment of the present invention.
Figure 2:
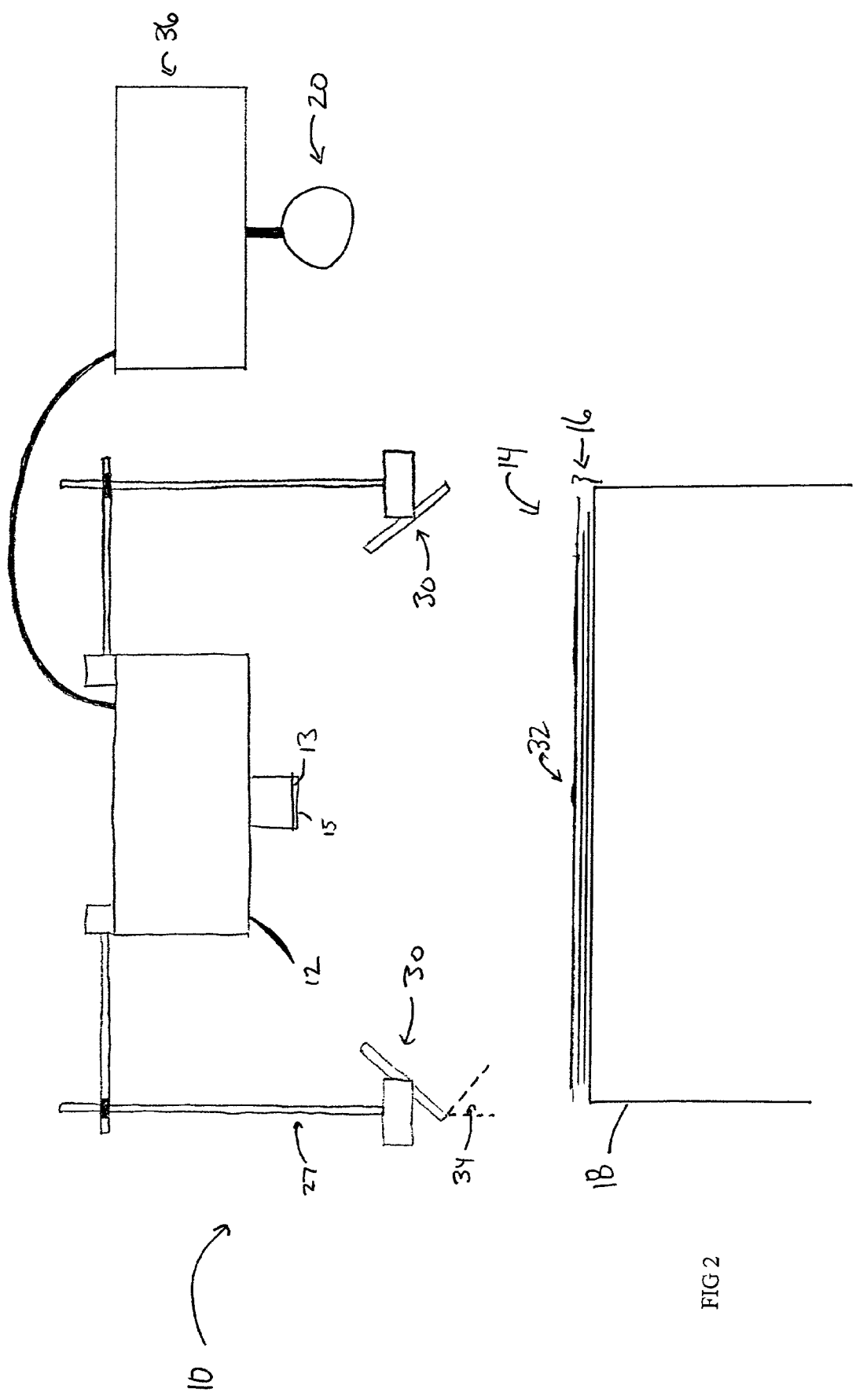
FIG. 2 is an alternative embodiment of a system for identifying defects in a composite structure according to the present invention.
Figure 3:
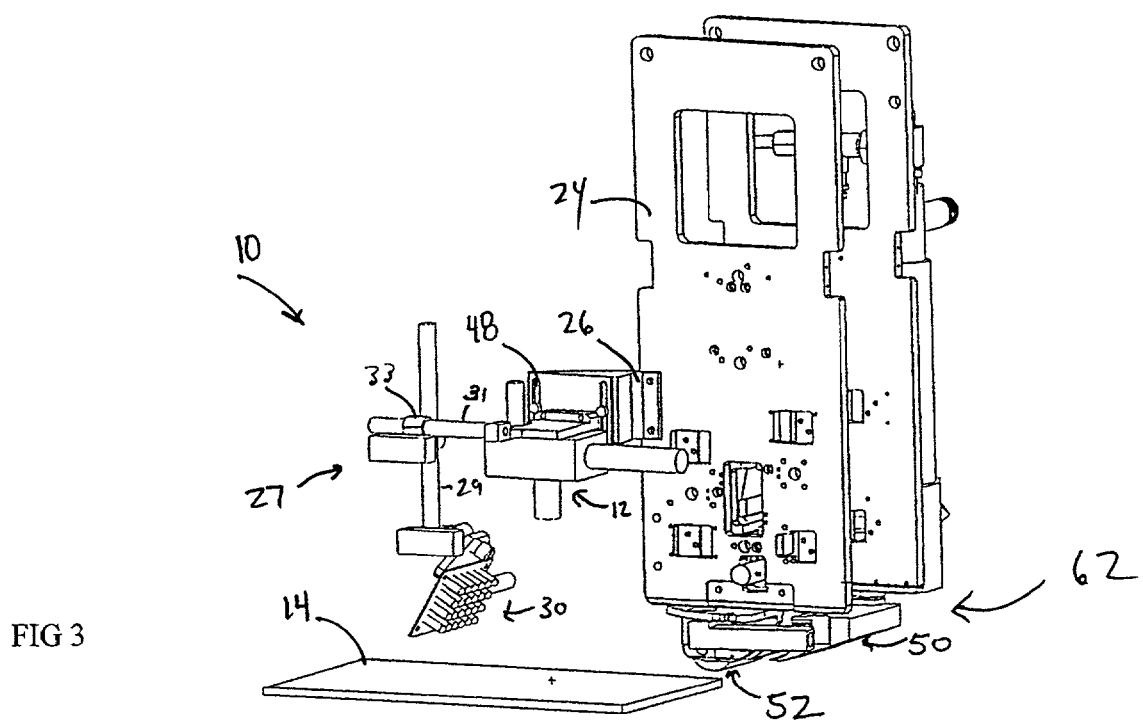
FIG. 3 is a perspective view of a portion of a system for identifying defects according to one embodiment of the present invention which is attached to a fiber placement device.

Turning first to FIGS. 1–3, a system for identifying defects in a composite structure according to the present invention is generally referred to as numeral 10. The system 10 is positioned proximate a composite structure 14, which is comprised of a plurality of adjacent tows or strips 16 of composite tape. The strips 16 typically include a plurality of fibers embedded in a resin or other material that becomes tacky or flowable upon the application of heat. The strips 16 are arranged on a work surface, such as a table, mandrel, or other tool 18, and compacted to form the composite structure 14 according to an automated collation technique, which is known in the art. For example, an article entitled "Material Selection/Fabrication Issues for Thermal Plastic Fiber Placement" by Richard Sharp et al. published in the "Journal of Thermoplastic Composite Materials" (January 1995) discusses one conventional fiber placement process and is incorporated herein by reference.

In general, the system 10 comprises a camera 12, a light source 30, and a processor and/or a memory device. The camera 12 is positioned proximate the composite structure 14 so as to capture an image of a predetermined portion of the composite structure, typically immediately downstream of the nip at which a composite tow is joined with the underlying structure. The light source 30 is also positioned proximate the composite structure 14 and the camera in such a way that light reflecting off defects in the composite structure creates visible images that can be captured by the camera 12. The camera 12 is, in turn, connected to a processor for interpreting the images, a storage device for storing the images, or both, as discussed more fully below.

The camera 12 can be a commercially-available camera capable of acquiring black and white images. For example, in one embodiment, the camera 12 is a television or other type of video camera having an image sensor (not shown) and a lens 13 through which light passes when the camera is in operation. Other types of cameras or image sensors can also be used, such as a fiber optic camera, Charge Coupled Device (CCD), or Complementary Metal Oxide Sensor (CMOS). The camera 12 can be positioned proximate the composite structure 14 on a stand (not shown) or mounted to a frame 24 or similar device. In one embodiment, the camera 12 is positioned approximately six inches from the surface of the composite structure 14 and is mounted to the frame 24 by way of a bracket 26 and associated connectors.

In addition, a filter 15 can be placed on the lens 13 for filtering light in a particular manner. Specifically, the filter 15 is designed according to one embodiment to filter light such that only the infrared component of the light can pass into the camera. Thus, the filter 15 prevents ambient visible light from entering the camera 12 and altering the appearance of the captured image. Other methods of filtering light can also be used to achieve the same result. For example, the camera may be designed to include a built-in filter of equivalent optical characteristics. In addition, the filter can be located between the camera lens 13 and image sensor. Alternatively, the camera may include an image sensor that is only sensitive in the infrared spectrum, thus eliminating the need for the filter.

The bracket 26 includes at least one slot 48 for allowing the camera 12 to be altered in a position relative to the composite structure 14 and secured in the desired position by a conventional nut and bolt combination. The frame 24, in turn, can be connected to a rolling mechanism (not shown) so that the camera 12 can be moved about the composite structure to capture images of different portions of the composite structure. However, the camera 12 and frame 24 can also be stationary, while the composite structure 14 is moved in relation thereto.

The system 10 also includes a unique light source 30 that illuminates the composite structure 14 such that defects 32 on or in the surface of the composite structure 14 can be detected by the camera 12. The light source 30 is positioned at an oblique angle 34 relative to the composite structure 14. In one embodiment, the oblique angle 34 is about 45°, although other angles are possible depending on the application. In addition, the light source 30 should also be positioned such that the light is emitted substantially perpendicular to the direction of placement of the strips 16. Specifically, the strips 16 of a particular layer are positioned in a common direction, and the light source 30 should be positioned about 90° to the common direction of the strips in order to highlight the defects 32, as discussed below. Further, the system 10 may include more than one light component. For example, the embodiment of FIG. 2 includes two light components positioned on either side of the camera 12 at oblique angles, again about 45° each, relative to the composite structure.

The light source 30 is adjustably positioned relative to the composite structure as described above by mounting or attaching the light source to a mounting apparatus 27, which as shown in FIGS. 1–3 can include a main shaft 29, a secondary shaft 31, and a locking clamp 33 for quickly and accurately adjusting the position of the light source. The mounting apparatus 27, in turn, can be attached to the frame 24, to the camera 12, or to some other object that defines a common position for both the light source and the camera such that the light source and camera maintain a constant spatial relationship relative to one another. In addition to positioning the light source at an oblique angle, such as 45°, relative to the composite structure 14, the mounting apparatus preferably positions the light source 30 perpendicular to the direction of travel of the system 10 (and thus perpendicular to the direction of placement of the strips as mentioned above) relative to the composite structure in order to illuminate the surface of the composite structure in the direct line of vision of the camera 12.

A common problem in conventional machine vision systems is the inability to effectively illuminate and then to detect particular defects, such as dark flaws on a dark background. In particular, the quality and magnitude of the surface illumination of the composite structure is greatly affected by ambient lighting and by the reflectivity of the material. In order to effectively illuminate a dark flaw on a dark background, the system of the present invention advantageously employs an infrared light source. In this regard, the light source 30 can be selected from an infrared light or another type of light, such as an incandescent light, having an infrared component. In this regard, power levels in the range of about 5W–25W in the wavelength range of about 700 nM–1000 nM are sufficient. In one particularly advantageous embodiment shown in FIG. 3, the light source 30 comprises a light emitting diode (LED), and in particular can include a plurality of LEDs arranged in an array or cluster formation. In one embodiment, the light source 30 includes 24 LED's mounted in an array upon a three-inch square printed circuit board. As a result of the infrared illumination, the LED array increases the contrast between the composite structure and a defect 32 relative to conventional systems. In another embodiment, the light source 30 includes incandescent light fiber that emits light optically piped from a remote source (not shown) to an array or arrays.

It has been observed that the composite structure 14 produces high glare when illuminated obliquely across the direction of placement of strips 16, while producing substantially less glare when illuminated obliquely along the direction of placement of the strips. While conventional systems sought to eliminate the glare, the systems and methods of the present invention seek to exploit the glare. In particular, the systems and methods of the present invention exploit the high-glare/low-glare phenomenon by casting oblique light across the top layer of composite strips in a direction substantially perpendicular to the direction of placement of the strips, which produces a relatively large amount of glare on the top layer. The underlying layers, which produce significantly less glare than the top layer because of their orientation, will show through any gaps or other defects in the top layer and thus be easily located. In addition, twists and other surface defects in the top layer will alter the orientation of the strips in the top layer and thus the glare of the top layer at the defect location.

Further, while the high-glare/low-glare phenomenon occurs when illuminated with either visible light or infrared light, the filter 16 used in one embodiment of the system 10 substantially removes the glare caused by ambient light such that only the glare caused by the infrared light source is used to locate the defects 32. Accordingly, the filter 16 removes the interference of ambient light as the composite structure is examined for defects.

The system 10 can also include a marking device 38 for indicating the location of the defects 32 on the composite structure 14. The marking device 38, which in one embodiment is an inkjet marking system, is attached to the frame 24 and is triggered by a processor 20 or similar device when a defect 32 is detected that is to be reported to the operator. In particular, the marking device 38 can spray a small spot of compatible ink of a highly visible color onto the surface of the composite structure 14 at the defect location to permit rapid access for repair and disposition. Other marking methods could also be used, such as audio or visual alerts and the like.

As shown in FIG. 3, the automated collation process includes guiding the composite strips 16 from material creels (not shown) to an automated collation or fiber placement machine 62, which is known in the art. For example, such machines are made by Cincinnati-Milacron and Ingersoll Milling Machines. In particular, the composite strips 16 are guided to a head unit 50 and fed under a compaction roller 52. Focused heat energy is then applied to the incoming material and the underlying material that was previously laid to adhere the two materials. With the combination of pressure and heat, the composite strip 16 is consolidated into the previous layer, thus forming an additional layer of the composite structure 14. Unfortunately, defects 32 may sometimes occur during the placement of the composite strip 16 onto the underlying composite structure 14. For example, in the case of fiber placement a gap may form between adjacent composite strips or a twist may occur in a composite strip during placement.

Figure 4:
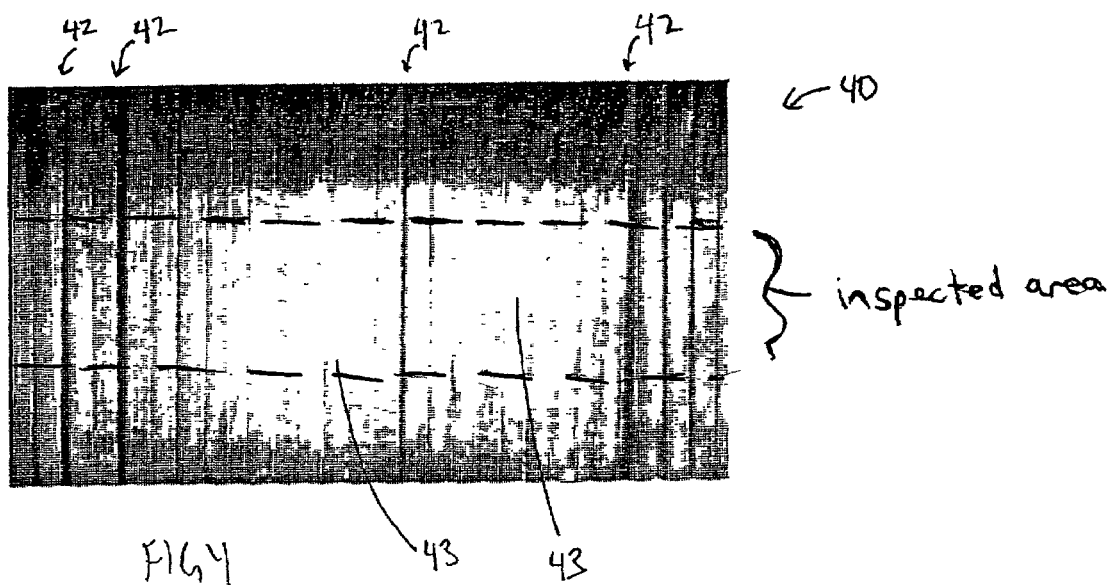
FIG. 4 is a graphical view of a computer readout for identifying defects in a composite structure according to one embodiment of the present invention.

According to one embodiment of the present invention, as the head unit 50 moves across the composite structure 14 and the composite strips 16 are laid down, the camera 12, which along with the light source 30 can be mounted to the head unit 50 according to one embodiment, continuously captures images of the structure and the strips. If the composite structure 14 is not planar, the inspection point should be as close to the nip point as possible. If the composite structure 14 is planar, the inspection point can be located without respect to the placement head unit 50. The images can be stored in a memory device 36 for future analysis and/or processed immediately by the processor 20, as discussed more fully below. FIG. 4 shows an example of an unprocessed camera image 40 which comprises a plurality of pixels having a range from black through a plurality of shades of gray to white. In particular, the unprocessed camera image 40 illustrates a contrast between a potential defect, such as a gap between the composite strips 16, and the remaining portions of the composite structure 14 that are defect free. As shown in FIG. 4, potential defects are shown as black or gray areas 42, while the remaining portions of the composite structure 14 remain substantially white 43. However, the potential defects need further processing to determine if the potential defects are acceptable or unacceptable, as discussed below. In addition, only a predetermined area of the camera image is inspected in order to minimize interference.

The processor 20 receives the images 40 from the camera 12 or from the memory device 36 in which the images have first been stored. The processor 20 and memory device 36 can be components of a conventional computer, such as an IBM-style PC or Apple-based MAC. The processor 20 manipulates the images to facilitate the reliable detection of defects.

Figure 5:
FIG. 5 is a graphical view of a binarized image of the graphical view of FIG. 4.

FIG. 5 shows a camera image 44, which is the same image as that depicted in FIG. 4 following binarization by the processor 20. In particular, all shades of gray above a predetermined threshold value have been changed to white, while all gray shades below the threshold have been changed to black to heighten the contrast of the defect 32 and improve the accuracy of detection. Advantageously, the system also includes a user interface 46 that is in communication with the processor 20. The user interface 46, such as a touch screen display driven by the processor 20, provides user controls 66 for adjustment of the binarization threshold. Typically, the setting of the binarization threshold involves a tradeoff between the sensitivity with which defects are detected and the resolution with which the defects are depicted. Typically, however, the binarization threshold is set to about 150 on a scale of 0 to 255. The interface 46 may also provide other controls, as discussed below.

Figure 6:
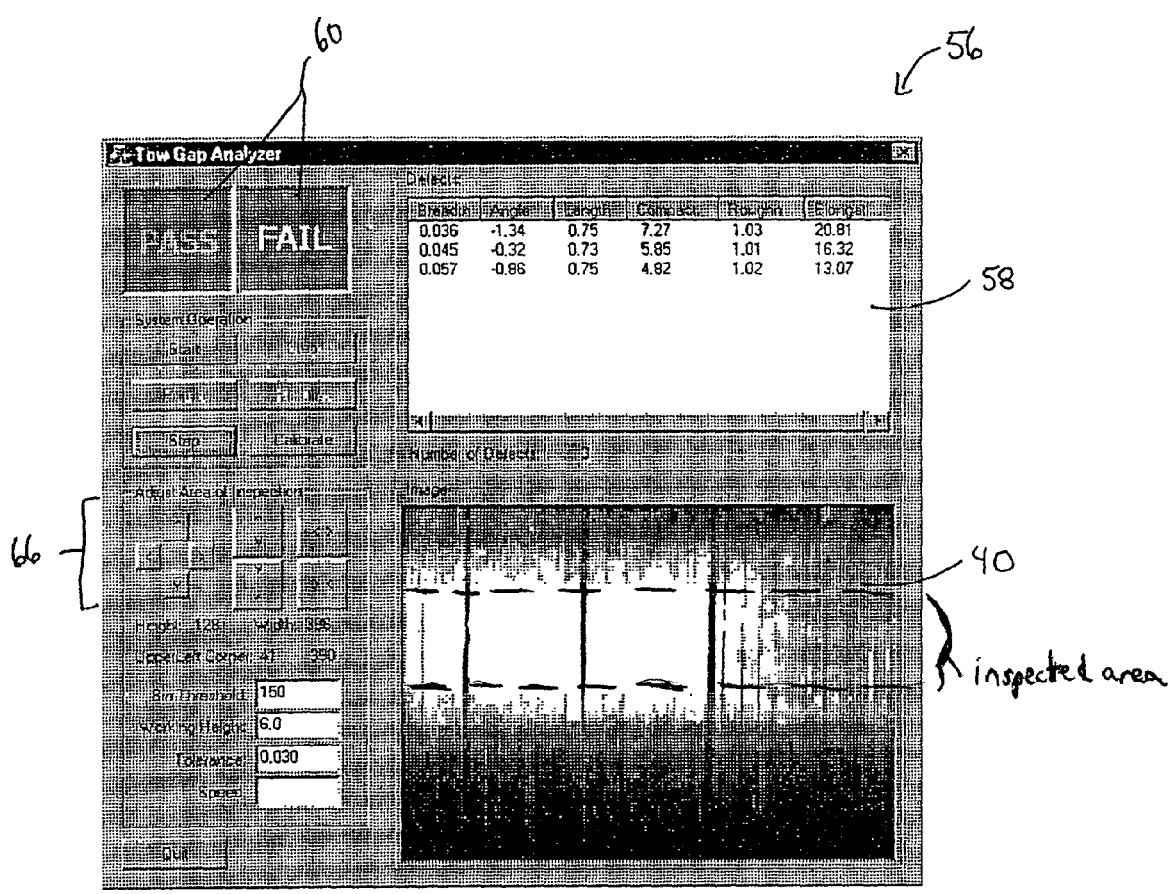
FIG. 6 is a graphical view of a computer display and selected user controls according to one embodiment of the present invention.

FIG. 6 shows one embodiment of a portion of the user interface 46 according to the system 10 of the present invention. The user interface 46 can run off many software applications, such as Windows 98, Windows/NT, Windows 2000, Windows CE, and equivalents. The user interface 46 also includes a display screen 56, such as on a computer monitor, and can also include a keyboard and mouse (not shown) for permitting an operator to move a cursor about the display screen 56 and input the binarization threshold, the area of inspection, and the acceptable tolerances of the maximum allowed defect width, such as +/−0.030 inch of the detected defect 32. The display screen 56 could also be touch-sensitive for permitting the operator to input the desired settings by manually pressing regions of the display screen. As shown in FIG. 6, an image of the composite structure 14, which can be the unprocessed camera image 40 or the binarized camera image 44, is displayed for viewing by the operator. In addition to the displayed image of the composite structure 14, the display screen 56 also includes a defect table 58 which lists the discovered defects 32 and provides information for each defect, such as location, size, and the like. The display screen 56 can also include status indicators 60 that display whether a particular image area is acceptable or not acceptable based on predefined criteria, such as the tolerances discussed above.

Thus, the present invention provides an improved system and method 10 for identifying defects 32 in a composite structure 14 by providing an obliquely-mounted light source 30 having an infrared component such that defects, and in particular defects that are oftentimes not detected by conventional systems such as dark defects on a dark background, can be identified. As a result, the system and method of the present invention permit the operator to quickly identify and correct defects 32 which would otherwise create structural flaws or inconsistencies that may affect the integrity of the composite structure 14. As such, less material is wasted, less labor is expended in inspection, and less machine down time is incurred during the fabrication process; therefore, a lower cost composite structure is achieved on average.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A system for identifying defects in a composite structure during fabrication thereof, comprising:
    a camera for receiving images of the composite structure comprised of a layer formed of a plurality of adjacent composite strips of material, wherein the plurality of adjacent composite strips are positioned in a common direction;
    a processor for processing said images and outputting a response identifying a defect based on said images; and
    a light source positioned at an oblique angle relative to the composite structure for illuminating the composite structure, said light source having an infrared component that is differently reflected by defects in the composite structure than from portions of the composite structure that are defect free, said light source being positioned to illuminate the composite structure in a direction substantially perpendicular to the common direction of the composite strips.

2. A system according to claim 1, wherein said light source is an incandescent light with an infrared component.

3. A system according to claim 1, wherein said camera is selected from the group consisting of a video camera and a fiber optic camera.

4. A system according to claim 1, further comprising a filter for preventing substantially all ambient visible light from entering the camera.

5. A system according to claim 1, wherein said light source comprises a plurality of light emitting diodes.

6. A system according to claim 5, wherein said light emitting diodes are arranged in a cluster formation.

7. A system according to claim 1, wherein the light source has a power output in the range of about 5W–25W.

8. A system according to claim 1, wherein said light source includes incandescent light fiber.

9. A system according to claim 1, wherein said light source comprises two arrays positioned such that an acute angle is defined therebetween.

10. A system according to claim 1, wherein said oblique angle is about 45°.

11. A system according to claim 1, further comprising a marking device for indicating said defects on the composite structure.

12. A system according to claim 11, wherein said marking device is an inkjet sprayer.

13. A system according to claim 1, wherein said camera is capable of capturing images having a plurality of pixels, said images ranging from black through a plurality of shades of gray to white.

14. A system according to claim 13, wherein said processor is capable of binarizing said images by setting all pixels representing a color darker than a predetermined gray level to one of black or white and setting all other pixels to the other of black or white.

15. A system according to claim 14, further comprising an interface for permitting an operator to set a threshold representative of the predetermined gray level utilized by said processor to binarize the images.

16. A system according to claim 1, wherein the composite structure comprises a plurality of composite strips, said composite strips being laid down by an automated collation process in which said composite strips are provided by a head unit and compacted to the underlying composite structure by a compaction roller, and wherein said camera and said light source are proximate the compaction roller.

17. A system according to claim 16, wherein said camera and said light source are mounted on said head unit.

18. A system for identifying defects in a composite structure during fabrication thereof, comprising:
    a camera for receiving images of the composite structure comprised of a layer formed of a plurality of adjacent composite strips, wherein the plurality of adjacent composite strips are positioned in a common direction;
    a memory device for storing said images; and
    a light source positioned at an oblique angle relative to the composite structure for illuminating the composite structure, said light source have an infrared component that is differently reflected by defects in the composite structure than from portions of the composite structure that are defect free, said light source being positioned to illuminate the composite structure in a direction substantially perpendicular to the common direction of the composite strips.

19. A system according to claim 18, wherein said light source is selected from the group consisting of an infrared light and an incandescent light.

20. A system according to claim 18, wherein said camera is selected from the group consisting of a video camera and a fiber optic camera.

21. A system according to claim 18, further comprising a filter for preventing substantially all ambient visible light from entering the camera.

22. A system according to claim 18, wherein the camera is capable of distinguishing light from the light source and ambient visible light.

23. A system according to claim 18, wherein said light source comprises a plurality of light emitting diodes.

24. A system according to claim 23, wherein said light emitting diodes are arranged in a cluster formation.

25. A system according to claim 18, wherein the light source has a power output in the range of about 5W–25W.

26. A system according to claim 18, wherein said light source comprises two arrays positioned such that an acute angle is defined therebetween.

27. A system according to claim 18, wherein said oblique angle is about 45°.

28. A system according to claim 18, further comprising a marking device for indicating said defects on the composite structure.

29. A system according to claim 28, wherein said marking device is an inkjet sprayer.

30. A system according to claim 18, wherein said camera is capable of capturing images by setting all pixels representing a color darker than a predetermined gray level to one of black or white and setting all other pixels to the other of black or white.

31. A system according to claim 18, wherein the composite structure comprises a plurality of composite strips, said composite strips being laid down by an automated collation process in which said composite strips are provided by a head unit and compacted to the underlying composite structure by a compaction roller, and wherein said camera and said light source are proximate the compaction roller.

32. A system according to claim 31, wherein said camera and said light source are mounted on said head unit.

33. A method of identifying defects in a composite structure during fabrication thereof, comprising:
    positioning a camera proximate the composite structure, wherein the composite structure is comprised of a layer formed of a plurality of adjacent composite strips that are positioned in a common direction;
    illuminating the composite structure with an obliquely-mounted light source having an infrared component, wherein illuminating the composite structure comprises illuminating the composite structure in a direction substantially perpendicular to the common direction of the composite strips;

moving the camera and light source across the composite structure;

recording images of the composite structure; and processing the images to identify defects in the composite structure.

34. A method according to claim 33, further comprising marking the defects on the composite structure.

35. A method according to claim 33, wherein illuminating the composite structure comprises illuminating the composite structure with a light selected from the group consisting of an infrared light and an incandescent light.

36. A method according to claim 33, wherein positioning the camera comprises positioning a fiber optic camera perpendicular to the composite structure.

37. A method according to claim 33, wherein processing the images comprises converting the images into dichotomous representations above or below a desired threshold.

38. A method according to claim 35, wherein illuminating the composite structure comprises illuminating the work surface with two arrays of lights.

39. A method according to claim 33, further comprising preventing substantially all ambient visible light from entering the camera.

* * * * *